United States Patent
Lopez et al.

(10) Patent No.: US 8,192,421 B2
(45) Date of Patent: Jun. 5, 2012

(54) MALE LUER LOCK CONNECTOR

(75) Inventors: Georges-Antoine Lopez, Craponne (FR); Patrick Delorme, Chaponost (FR); Ludovic Allard, Millery (FR)

(73) Assignee: Ace Development Solution (FR)

( * ) Notice: Subject to any disclaimer, the term of this patent is extended or adjusted under 35 U.S.C. 154(b) by 685 days.

(21) Appl. No.: 12/299,040

(22) PCT Filed: May 22, 2007

(86) PCT No.: PCT/FR2007/051308
§ 371 (c)(1),
(2), (4) Date: Oct. 30, 2008

(87) PCT Pub. No.: WO2007/135337
PCT Pub. Date: Nov. 29, 2007

(65) Prior Publication Data
US 2009/0105692 A1    Apr. 23, 2009

(30) Foreign Application Priority Data
May 24, 2006    (FR) ..................................... 06 04659

(51) Int. Cl.
*A61M 25/16* (2006.01)
*A61M 25/18* (2006.01)
*A61M 39/00* (2006.01)
*A61M 39/10* (2006.01)

(52) U.S. Cl. ..................................................... 604/533
(58) Field of Classification Search ........... 604/533–539
See application file for complete search history.

(56) References Cited

U.S. PATENT DOCUMENTS

| | | | | |
|---|---|---|---|---|
| 3,548,827 A | * | 12/1970 | Abel | 604/318 |
| 4,875,718 A | * | 10/1989 | Marken | 285/148.15 |
| 5,549,583 A | * | 8/1996 | Sanford et al. | 604/535 |
| 6,059,325 A | | 5/2000 | Heckele et al. | |
| 6,419,699 B1 | * | 7/2002 | Schuessler | 623/11.11 |
| 2006/0005840 A1 | | 1/2006 | Cannon | |
| 2006/0033334 A1 | | 2/2006 | Weber et al. | |
| 2008/0249508 A1 | | 10/2008 | Lopez et al. | |

FOREIGN PATENT DOCUMENTS

| | | |
|---|---|---|
| DE | 8321694 U1 | 11/1983 |
| DE | 3737665 A1 | 5/1989 |
| EP | 1236481 B1 | 10/2004 |
| FR | 2861311 A | 4/2005 |

OTHER PUBLICATIONS

International Search Report for PCT/FR2007/051308, dated Sep. 14, 2007.

* cited by examiner

*Primary Examiner* — Kevin C Sirmons
*Assistant Examiner* — Andrew Gilbert
(74) *Attorney, Agent, or Firm* — Victor A. Cardona; Heslin Rothernberg Farley & Mesiti P.C.

(57) ABSTRACT

Connector for medical use comprising: a body joined to a line or adapted to be connected at one of its ends to a tubing in which a fluid flows, and a male luer lock connection comprising a base mounted rotatingly on the body and cooperating by friction with it, without any possible translational movement. The base is joined to a hollow tubular body, having a threaded inner surface and a male central luer cone. The outer surface of the body and the inner surface of the base of the connection, cooperating by friction, have a spherical then cylindrical shape.

8 Claims, 2 Drawing Sheets

MALE LUER LOCK CONNECTOR

CROSS REFERENCE TO RELATED APPLICATIONS

This application is a national stage filing under section 371 of International Application No. PCT/FR2007/051308, filed on May 22, 2007, and published in French on Nov. 29, 2007 as WO 2007/135337 A1 and claims priority of French application No. 0604659 filed on May 24, 2006, the entire disclosure of these applications being hereby incorporated herein by reference.

The invention relates to a connector for medical use. It relates more particularly to a male luer lock connector intended to cooperate with a female luer connector in order to connect a liquid line.

Two types of luer lock connector are available on the market today.

The first range consists of connectors in which a male luer lock connection is mounted rotatingly on a tubular body joined to the fluid inlet tubing. In this type of connector, the connection cannot move translationally, and can only rotate. In practice, the connection is provided with a thread for screwing to the female luer end piece. To guarantee the tightness, an O-ring is positioned between the inner surface of the connection and the outer surface of the body. This form of connector is described for example in document DE 373 76 65.

The other range of connectors is for example the one illustrated in document EP-A-1 236 481. Unlike the luer lock connectors described above, the connection here does not only rotate about the tubular body but also moves translationally along the body. A stop is arranged on the body in order to limit the travel of the ring and consequently its separation from the body. The connection to the female luer is also provided by screwing. This type of connector has a major drawback: when tightened, that is when the male luer and the female luer are joined together, the mobile ring tends to loosen because of the stress between the internal threads of the ring and the stop limiting its translational movement. In other words, the ring tends to unscrew and then no longer performs its locking function. This incurs a risk of leaks, or even of disconnection.

It is the object of the present invention to improve the first range of connectors. The devices described in document DE 373 76 65 have a number of drawbacks. Firstly, the risk of disconnection of the male luer from the body subsists. This is because in this document, the male luer connection is joined to the body by clipping the male luer connector using a band arranged on the whole periphery of the body. According to the pressure applied in the connector, the system may be disconnected because of the rounded shape of the said band. Moreover, the cost of this type of product is high due to the presence of three parts, respectively a body, a connection and a seal.

In other words, the problem that the invention proposes to solve is to develop a luer lock connector that has no seal, in order to decrease the cost of the product, but which nevertheless remains perfectly leaktight without any risk of disconnection of the ring from the body.

To solve this problem, the Applicant has developed a specific body shape, cooperating by friction with a matching shape arranged at the end of the connection, in the absence of any seal.

BRIEF SUMMARY OF THE INVENTION

More precisely, the invention relates to a connector for medical use comprising:

a body joined to a line or intended to be connected at one of its ends to a tubing in which a fluid flows, a male luer lock connection comprising a base mounted rotatingly on the body and cooperating by friction with it, without any possible translational movement, the base being joined to a hollow tubular body, whereof the inner surface is provided with a thread and whereof the centre is provided with a male luer cone.

This connector is characterized in that it has no seal and in that the outer surface of the body and the inner surface of the base of the connection, cooperating by friction, have a spherical then cylindrical shape.

According to the invention, the connector body is joined to a line or is suitable for connection to a line. In the first case, reference is made to ramps, valves or Y-piece connectors whereof the end directly has the shape of the body of the connector of the invention. The second case hypothesises that the body of the connector of the invention is connected by adhesive to a flexible tubing in which a fluid flows.

The essential feature of the connector is to have a spherical then cylindrical shape in the body and the base of the connection.

Whether the connector is used for perfusion, which accounts for most of the cases, or for sampling, the spherical then cylindrical zones may be arranged in any direction towards the terminal end of the body. This spherical part may be followed by the cylindrical part or vice versa. Regardless of the shape of the body, the base of the male luer lock connection has a matching shape cooperating by friction with the matching shape of the body.

The connectors in which the body has a spherical then cylindrical shape in the direction of its free terminal end are more particularly described below.

When the connector is intended for connection to a flexible tubing, the spherical zone of the body is preceded by a linkage zone whereof the outer surface has any shape, generally conical or cylindrical. In this case, the flexible tubing is connecting in the channel formed at the centre of the linkage zone. In practice, the linkage zone is cylindrical and has a diameter $d_5$, lower than the diameter $d_1$ of the spherical portion of the body.

When the connector is joined to a ramp, a valve or a Y-piece connector, the spherical then cylindrical parts are moulded directly at the time of their fabrication.

The various embodiments of the body and the matching connection will now be described in greater detail.

In a first embodiment, the outer surface of the body has at least two successive lengths, respectively:

a first length in the form of a portion of sphere having diameter $d_1$, a second cylindrical length having diameter $d_2$ lower than $d_1$, the inner surface of the base having:

a first zone in the form of a portion of sphere having a diameter $d_7$ substantially equal to $d_1$, a second tubular zone, having a diameter $d_3$ slightly lower than $d_2$.

In this case, the seal and hence the clamping of the connection to the connector body is provided by close contact between the cylindrical length of the body and the matching cylindrical length of the base of the connection, whereof the diameter $d_3$ is slightly lower than $d_2$ in order to be force fitted into one another. The spherical zone performs the function of joining and clipping the body to the base.

In an advantageous embodiment:

the outer surface of the body has at least three successive lengths, respectively:

a first cylindrical length having diameter $d_4$, a second length in the form of a portion of sphere, the diameter $d_4$ being substantially equal to the diameter $d_1$ of the largest cross section of the portion of sphere, a third cylindrical length having diameter $d_2$ lower than $d_1$, the inner surface of the base has:

a first zone in the form of a portion of sphere having diameter $d_7$ substantially equal to $d_1$, a second tubular zone having diameter $d_3$ slightly lower than $d_2$.

In this case, the connector has two leaktight zones. The first leaktight zone is provided by the close contact between the third cylindrical length and the matching cylindrical length of the base of the connection, whereof the diameter $d_3$ is slightly lower than $d_2$. The second leaktight zone is provided by the close contact between the edge of the first cylindrical length having diameter $d_4$ of the body and the spherical shape of the base having diameter $d_1$. The spherical zone preserves its original function of joining and clipping.

Regardless of the embodiment of the connector, the spherical zone of the base may be preceded by an advantageously tubular zone having inside diameter $d_6$ lower than $d_1$, this zone being intended to clamp either the line of the ramp or the linkage zone having diameter $d_5$ of the connector when the latter is arranged at the end of a flexible tubing. In practice, $d_5$ is lower than or equal to $d_6$.

BRIEF DESCRIPTION OF THE DRAWING FIGURES

The invention and the advantages thereof will appear more clearly from the following exemplary embodiments, in conjunction with the appended figures.

DETAILED DESCRIPTION

Figure 1:
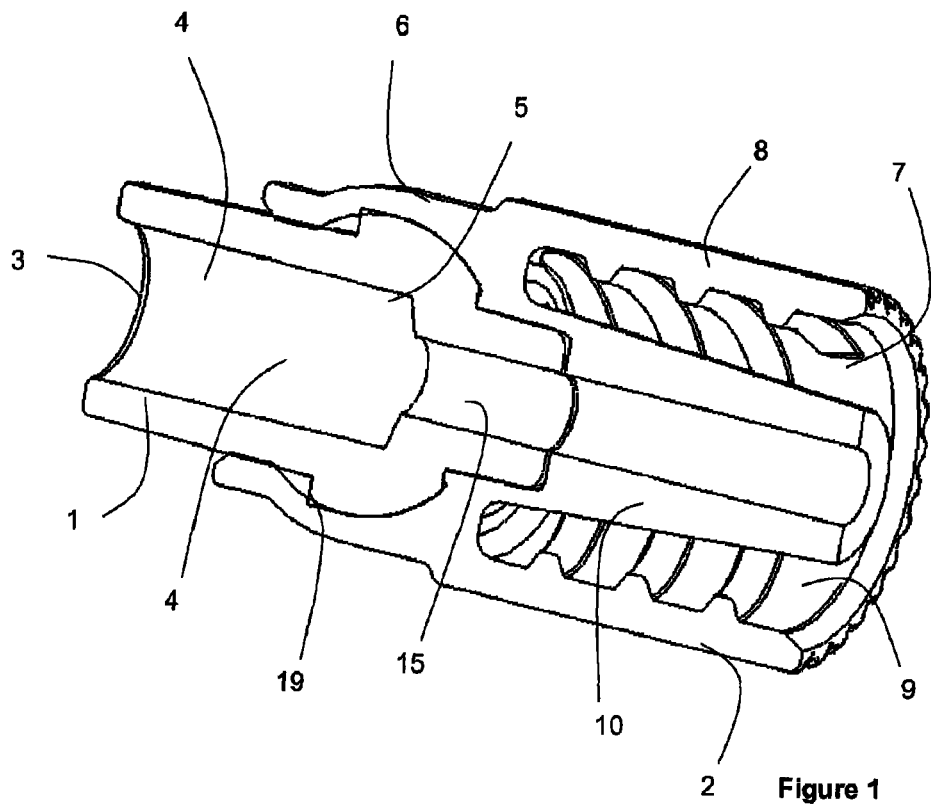
FIG. 1 shows a cross section of the connector of the invention.

FIG. 1 shows a male luer lock connector like the one of the invention. This connector consists of two distinct parts, respectively a body (1) and a male luer connection (2).

The body (1) is suitable for connection by its end (3) to a fluid tubing not shown. In practice, the fluid tubing is connected to the body by fitting and then bonding in the channel (4). At its opposite end (5), the body cooperates by friction with the base (6) of the connection (2). In practice, the contact applied between the inner surface of the base (6) and the outer surface of the terminal end (5) of the body (1) causes the rotation of the connection about the body without any possibility of translational movement. In its terminal portion, the male luer connection is a conventional coupling consisting of a hollow body (7) comprising a wall (8), whereof the inner surface (9) is provided with a thread for screwing and hence locking the female luer after connection. The hollow body further comprises a central conical male luer channel (10).

Figure 2:
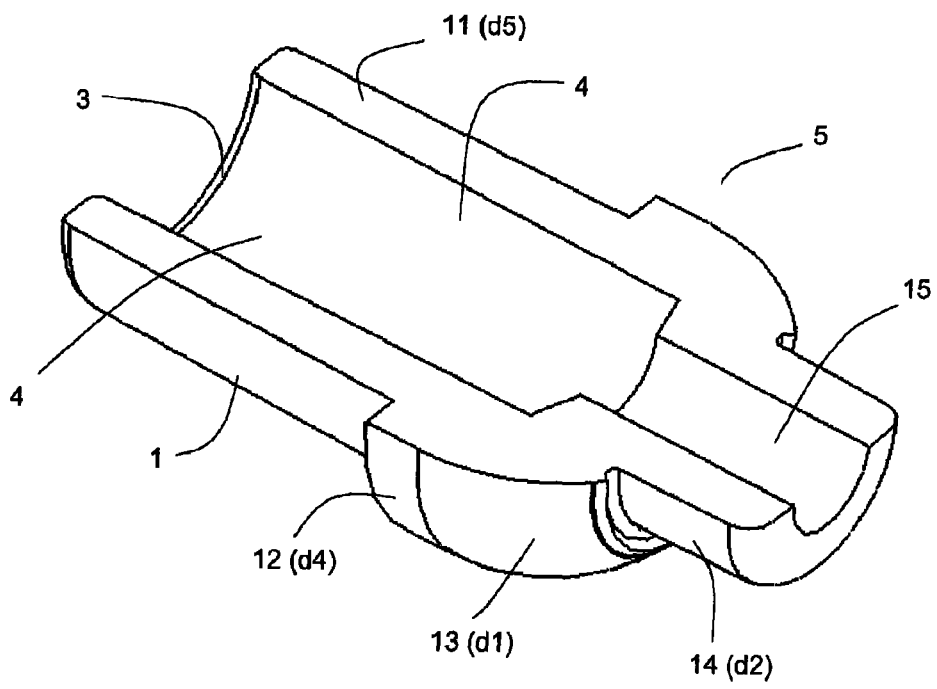
FIG. 2 shows a cross section of the body.

FIG. 2 shows a cross section of the body (1). According to the invention, this body has four distinct successive zones, respectively, upstream, a zone called a linkage zone having an outer tubular surface (11) with diameter $d_5$, followed by a first cylindrical length (12) having outside diameter $d_4$ greater than $d_5$, then a second length (13) in the form of a portion of sphere having diameter $d_1$ of which the largest cross section is substantially equal to $d_4$, and a third length (14) having a tubular shape and a diameter $d_2$ lower than $d_1$.

As already stated, the body is provided at its centre with a channel (4) in which the fluid flows. This channel has a first cross section then a lower cross section (15) having a lower diameter, substantially equal to the cross section of the male luer channel (10).

The luer lock connection will now be described in detail.

Figure 3:
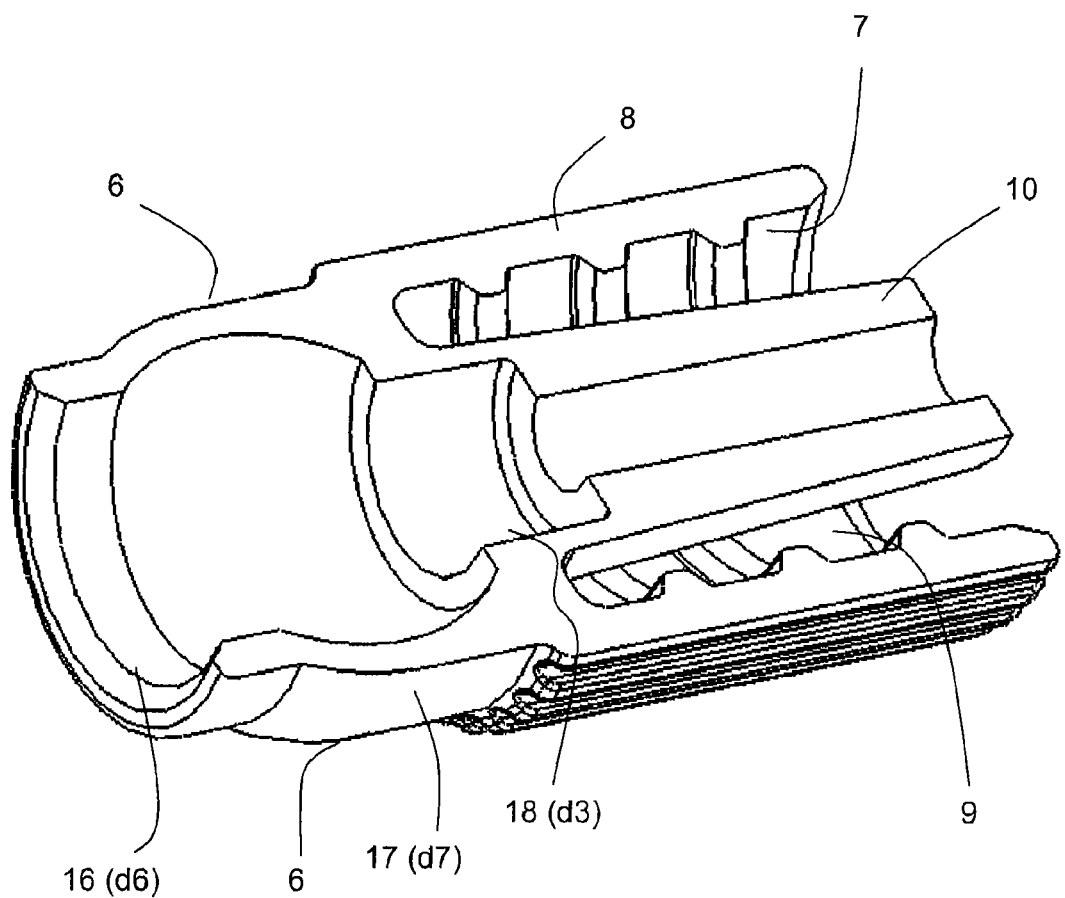
FIG. 3 shows a cross section of the connection.

As shown in FIG. 3, the base (6) has a first tubular zone (16), whereof the diameter of the inner surface $d_6$ is substantially equal to the diameter $d_5$ of the linkage zone of the body. Moreover, the base has a first length (17) having a spherical shape whereof the diameter $d_7$ is substantially equal to that of the largest cross section of the portion of sphere having diameter $d_1$ of the body. Finally, the base of the connection has a second tubular zone (18) having a tubular shape, whereof the diameter $d_3$ is substantially equal to that of the diameter $d_2$ of the body (1).

In this way, the clipping of the connection (2) to the body (1) creates two leaktight zones. The superimposition of the terminal cylindrical zone (14) of the body (1) with the matching zone (18) of the base ensures the primary seal of the system owing to the diameter of $d_3<d_2$ and hence of the force fitting of the two elements together. The interference zone existing between the edge (19) of the cylindrical zone (12) of the body and the spherical zone (17) of the base guarantees a secondary seal.

The invention and the advantages thereof will appear clearly from the above description. A friction zone may be observed in particular, having a specific shape and serving to guarantee the seal of the connector without any risk of disconnection and in the absence of a seal.

The invention claimed is:

1. A connector for medical use comprising:
    a body joined to a line or adapted to be connected at one end to a tubing in which a fluid flows,
    a male luer lock connection comprising a base mounted rotatingly on the body and cooperating by friction with the body, without any possible translational movement, the base being joined to a hollow tubular body, having a threaded inner surface and a central male luer cone,
    wherein the connector has no additional element that acts as a seal between the body and the base, and an outer surface of the body and an inner surface of the base cooperate by friction, the outer surface of the body having at least two successive lengths, respectively:
        a first length in the form of a portion of sphere having diameter $d_1$, and
        a second cylindrical length having diameter $d_2$ smaller than $d_1$; and
    the inner surface of the base having:
        a first zone in the form of a portion of sphere having a diameter $d_7$ substantially equal to $d_1$, and
        a second tubular zone, having a diameter $d_3$ slightly smaller than $d_2$; and
    wherein the outer surface of the body further includes an additional cylindrical length having diameter $d_4$, the additional cylindrical length preceding the first length, the diameter $d_4$ being substantially equal to the diameter $d_1$ of the largest cross section of the portion of sphere.

2. The connector according to claim 1, wherein the first zone is preceded by a tubular zone having diameter $d_6$ smaller than $d_1$.

3. The connector according to claim 1, wherein the first length is preceded by a linkage zone having a diameter $d_5$ and an outer surface of any shape.

4. A valve equipped with the connector of claim 1.

5. A ramp equipped with the connector of claim 1.

6. A Y-piece connector equipped with the connector of claim 1.

7. A perfusion tube equipped with the connector of claim 1.

8. An extension equipped with the connector of claim 1.

* * * * *